(12) United States Patent
Zhang et al.

(10) Patent No.: US 11,769,237 B2
(45) Date of Patent: Sep. 26, 2023

(54) MULTIMODAL MEDICAL IMAGE FUSION METHOD BASED ON DARTS NETWORK

(71) Applicant: HUAZHONG UNIVERSITY OF SCIENCE AND TECHNOLOGY, Hubei (CN)

(72) Inventors: Xuming Zhang, Hubei (CN); Shaozhuang Ye, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 18/001,295

(22) PCT Filed: Jan. 30, 2021

(86) PCT No.: PCT/CN2021/074531
§ 371 (c)(1),
(2) Date: Dec. 9, 2022

(87) PCT Pub. No.: WO2022/121100
PCT Pub. Date: Jun. 16, 2022

(65) Prior Publication Data
US 2023/0196528 A1    Jun. 22, 2023

(30) Foreign Application Priority Data

Dec. 11, 2020   (CN) .......................... 202011467496.5

(51) Int. Cl.
*G06T 5/50*      (2006.01)
*G16H 30/40*    (2018.01)
(Continued)

(52) U.S. Cl.
CPC ............... *G06T 5/50* (2013.01); *G06T 3/40* (2013.01); *G06T 3/60* (2013.01); *G06T 5/20* (2013.01);
(Continued)

(58) Field of Classification Search
CPC .................................. G06T 5/50; G16H 30/40
See application file for complete search history.

(56) References Cited

U.S. PATENT DOCUMENTS 9,922,272 B2   3/2018   Cheng et al.
2019/0156526 A1*   5/2019   Liu ........................... G06T 7/90
(Continued)

FOREIGN PATENT DOCUMENTS

CN   110852168 A   2/2020
CN   111553480 A   8/2020
(Continued)

OTHER PUBLICATIONS

International Search Report and Written Opinion issued in PCT/CN2021/074531, dated Sep. 23, 2021, 11 pages provided, English translation provided.

(Continued)

*Primary Examiner* — Yi Yang
(74) *Attorney, Agent, or Firm* — HAMRE, SCHUMANN, MUELLER & LARSON, P.C.

(57) ABSTRACT

A multimodal medical image fusion method based on a DARTS network is provided. Feature extraction is performed on a multimodal medical image by using a differentiable architecture search (DARTS) network. The network performs learning by using the gradient of network weight as a loss function in a search phase. A network architecture most suitable for a current dataset is selected from different convolution operations and connections between different nodes, so that features extracted by the network have richer details. In addition, a plurality of indicators that can represent image grayscale information, correlation, detail information, structural features, and image contrast are used as a (Continued)

network loss function, so that the effective fusion of medical images can be implemented in an unsupervised learning way without a gold standard.

19 Claims, 4 Drawing Sheets

(51) Int. Cl.
   *G06T 3/40* (2006.01)
   *G06T 3/60* (2006.01)
   *G06T 5/20* (2006.01)
   *G06V 10/80* (2022.01)
   *G06V 10/771* (2022.01)

(52) U.S. Cl.
   CPC .......... *G06V 10/771* (2022.01); *G06V 10/806* (2022.01); *G16H 30/40* (2018.01); *G06T 2207/20081* (2013.01); *G06T 2207/20221* (2013.01)

(56) References Cited

U.S. PATENT DOCUMENTS

| | | | |
|---|---|---|---|
| 2019/0304095 A1* | 10/2019 | Veni | G06T 7/174 |
| 2020/0034948 A1* | 1/2020 | Park | G06N 3/047 |
| 2020/0167930 A1* | 5/2020 | Wang | G06N 3/08 |
| 2021/0133926 A1* | 5/2021 | Jia | G06T 7/33 |
| 2021/0264256 A1* | 8/2021 | Zela | G06V 10/764 |

FOREIGN PATENT DOCUMENTS

| | | |
|---|---|---|
| CN | 111612754 A | 9/2020 |
| CN | 111882514 A | 11/2020 |

OTHER PUBLICATIONS

Gao et al., "Medical image fusion algorithm based on generative adversarial residual network", Journal of Computer Applications, Dec. 10, 2019, vol. 39, Issue 12, pp. 3528-3534, with English Abstract.

* cited by examiner

MULTIMODAL MEDICAL IMAGE FUSION METHOD BASED ON DARTS NETWORK

TECHNICAL FIELD

The present invention relates to the field of image fusion technologies in image processing and analysis, and more specifically, to a multimodal medical image fusion method based on a differentiable architecture search (DARTS) network.

BACKGROUND

With the development of medical imaging technology, more and more medical imaging techniques such as ultrasound imaging (US), computed tomography (CT), magnetic resonance imaging (MRI), positron emission tomography (PET), and single photon emission computed tomography (SPECT) have been applied to diagnosis and evaluation of diseases of various organs of the human body. Each medical imaging technique has advantages and disadvantages. For example, CT imaging covers all anatomical parts of the human body with high density resolution, but has low spatial resolution, poor joint and muscle display, and artifacts. MR imaging has high soft tissue resolution with no bone artifacts and overlap artifacts, but has the disadvantage of long scan time and lower spatial resolution than that of CT. Multimodal medical image fusion can integrate information specific to images with different modalities into one image, thereby facilitating observation and diagnosis by doctors. Therefore, multimodal medical image fusion plays an important role in clinical practice. For example, US and MRI are fused to implement prostate puncture biopsy, and PET and CT are fused to implement lung cancer detection.

The traditional image fusion algorithms mainly include pixel-level, feature-level, and decision-level fusion methods. Pixel-level fusion can obtain high accuracy and is simple to implement, but has poor anti-interference ability and is sensitive to noise and prone to artifacts in medical image fusion, thereby affecting the diagnostic accuracy of doctors. Feature extraction in feature-level fusion methods mainly depends on artificially designed methods, and it is difficult to adapt artificially designed features to different medical images due to the complexity of medical images. Decision-level fusion is insensitive to noise, but has poor fusion accuracy and is difficult to implement. In addition, the amount of information obtained from fused images is small, and important information may be lost during the use of decision-level fusion in medical image fusion.

Deep learning can learn feature information from a large number of samples, and has been widely used in image processing and analysis tasks such as image segmentation, image alignment, and image fusion in recent years. As for image fusion, in the absence of a gold standard, deep learning-based image fusion methods may be divided into the following two categories. In the first category, features are extracted by using a deep learning method, and then images are fused by using a conventional fusion strategy based on the extracted features. The second category involves end-to-end fusion methods, where an end-to-end network architecture is trained on image datasets using measures such as mean squared error (MSE) and structural similarity (SSIM).

The methods in the first category are simple to implement, and directly use a pre-trained model and some conventional fusion and reconstruction strategies for image fusion. However, the pre-trained model is generally applicable to a specific dataset. Therefore, this method has poor generalization and may be not applicable to multi-dataset or multi-task image fusion. In the methods in the second category, the design of the network architecture and the loss function of the network are crucial. Existing fusion methods in this category usually use simple network architectures such as convolutional neural network (CNN) and ResNet and simple measures such as MSE and SSIM, making it difficult to ensure the quality of fused images.

SUMMARY

In view of the deficiencies and improvement requirements in the prior art, the present invention provides a multimodal medical image fusion method based on a differentiable architecture search (DARTS) network, thereby improving image quality after multimodal medical image fusion.

To achieve the above objective, the present invention provides a multimodal medical image fusion method based on a DARTS network, comprising:

S1. performing a network architecture search on a preset DARTS model by using multimodal medical image data to obtain a DARTS network architecture applicable to the multimodal medical image data, wherein the DARTS network architecture comprises one or more cells connected in series, each cell comprises a plurality of nodes, each of the nodes is connected to outputs of two preceding cells or other nodes in a current cell by means of different convolution operations, and channels of the nodes are combined into an output of the cell;

S2. constructing a multimodal medical image fusion network, wherein the multimodal medical image fusion network comprises a multi-channel DARTS network module, a feature fusion module and an upsampling module. Here, the multi-channel DARTS network module is formed by a plurality of parallel DARTS network architectures, the DARTS network architecture is configured to downsample an input image to obtain a corresponding feature map, the feature fusion module is configured to perform feature fusion on a feature map outputted by a dual-channel DARTS network module, and the upsampling module is configured to perform convolution upsampling on a fused feature to obtain the fusion image with the same size as the input image;

S3. training the multimodal medical image fusion network by using the multimodal medical image data through an unsupervised learning method; and S4. inputting a multimodal medical image to be fused into a trained multimodal medical image fusion model to obtain a fusion result.

Further, structural similarity (SSIM), multi-scale structural similarity (MS-SSIM), edge preservation, sum of the correlations of differences (SCD), mutual information (MI), and structural representation-based mutual information (SR-MI) are used as a loss function for training the multimodal medical image fusion network.

Further, the loss function for training the multimodal medical image fusion network is:

$$\text{Loss} = (L_{SCD} + L_{MI}) + \lambda_1 \cdot (L_{SSIM} + L_{MS\text{-}SSIM} + L_{Q_g s_1 s_2/F}) + \lambda_2 \cdot L_{SR\text{-}MI},$$

where $L_{SSIM}$ represents an SSIM loss, $L_{SCD}$ represents an SCD loss, $L_{MI}$ represents an MI loss, $L_{MS\text{-}SSIM}$ represents an MS-SSIM loss, $L_{Q_g s_1 s_2/F}$ represents an edge preservation loss, $L_{SR\text{-}MI}$ represents an SR-MI loss, and $\lambda_1$ and $\lambda_2$ are weights of the groups of loss functions, respectively.

Further, the different convolution operations in step S1 comprise: a depthwise separable convolution with a convolution kernel size of 3, a depthwise separable convolution with a convolution kernel size of 5, a standard convolution with a convolution kernel size of 3, a standard convolution with a convolution kernel size of 5, a dilated convolution with a convolution kernel size of 3, a dilated convolution with a convolution kernel size of 5, and skip connections.

Further, the DARTS network architecture comprises one cell.

Further, the cell comprises four nodes.

Further, a convolution step size in the cell is set to 1, and a padding mode is used to make the feature map have a size consistent with that of the input image.

Further, the feature fusion module is configured to perform feature fusion on a feature map outputted by a dual-channel DARTS network module, and specifically fusion of the feature map is implemented by means of channel combination.

Further, the method further comprises performing data augmentation on the multimodal medical image data.

Further, the data augmentation comprises translation, rotation, and non-rigid deformation.

In general, compared with the prior art, through the foregoing technical solutions designed in the present invention, the following beneficial effects can be obtained:

In the present invention, feature extraction is performed on a multimodal medical image by using a differentiable architecture search (DARTS) network. The network performs learning by using the gradient of network weight as a loss function in a search phase. A network architecture most suitable for a current dataset is selected from different convolution operations and connections between different nodes, so that features extracted by the network have richer details. In addition, in the present invention, a plurality of indicators that can represent image grayscale information, correlation, detail information, structural features, and image contrast are used as a network loss function, so that effective fusion of medical images can be implemented in an unsupervised learning mode without a gold standard, and compared with existing methods, a better fusion effect is achieved in aspects such as preservation of image details and improvement of image contrast.

BRIEF DESCRIPTION OF THE DRAWINGS

FIG. 3(*a*) shows a source CT image used in an embodiment of the present invention and a compared method;

FIG. 3(*b*) shows a source MR image used in an embodiment of the present invention and a compared method;

FIG. 4(*a*) shows a fused image obtained through NSCT-SR in Compared Method 1;

FIG. 4(*b*) shows a fused image obtained through DTCWT-SR in Compared Method 2;

FIG. 4(*c*) shows a fused image obtained through NSST-PAPCNN in Compared Method 3;

FIG. 4(*d*) shows a fused image obtained through Dense-Fuse in Compared Method 4;

FIG. 4(*e*) shows a fused image obtained through VIFNet in Compared Method 5;

FIG. 4(*f*) shows a fused image obtained through Nestfuse in Compared Method 6.

DETAILED DESCRIPTION

To make the purpose, technical solution, and advantages of the present invention clearer, the present invention is further described in detail below in connection with the accompanying drawings and embodiments. It should be appreciated that the specific embodiments described here are used merely to explain the present invention and are not used to define the present invention.

In addition, the technical features involved in various embodiments of the present invention described below can be combined with each other as long as they do not constitute a conflict between them.

Figure 1:
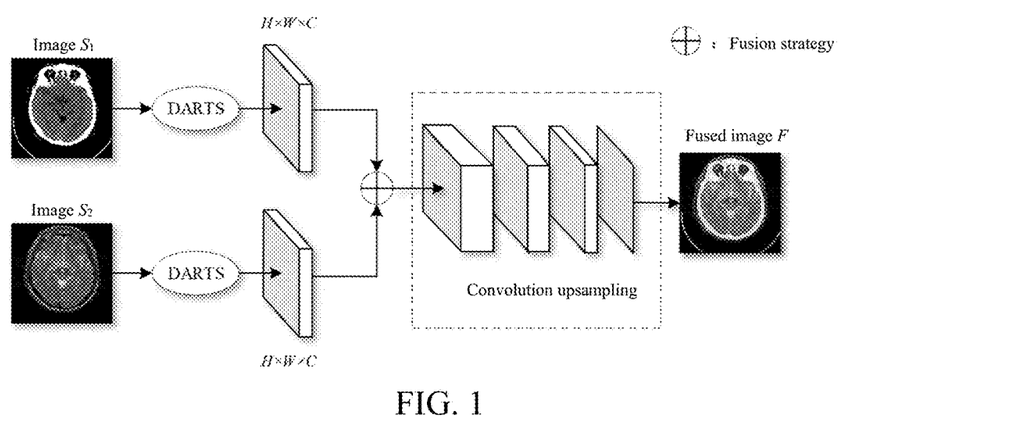
FIG. 1 is a structural diagram of a multimodal medical image fusion method based on a DARTS network according to the present invention.

Referring to FIG. 1, a multimodal medical image fusion method based on a DARTS network provided in the present invention includes the following steps:

S1. Performing a network architecture search on a preset DARTS model by using multimodal medical image data to obtain a DARTS network architecture applicable to the multimodal medical image data, wherein the DARTS network architecture includes a plurality of cells connected in series, each cell includes a plurality of nodes, each of the nodes is connected to outputs of two preceding cells or other nodes in a current cell by means of different convolution operations, and channels of the nodes are combined into an output of the cell.

Figure 2:
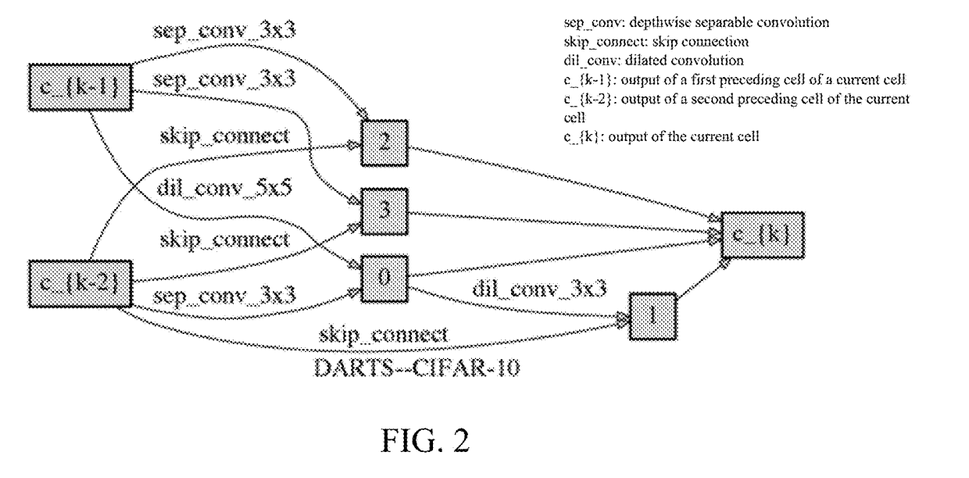
FIG. 2 shows a cell structure of a DARTS model in a CIFAR-10 dataset.

In the embodiments of the present invention, the DARTS network is a DARTS model pretrained by using a data set CIFAR-10. However, a fully connected layer part and a classifier part of the DARTS network are removed. To ensure the extraction of image features and at the same time greatly reduce network parameters, a quantity of cells is set to 1, and a quantity of nodes in each cell is set to 4. A specific structure is shown in FIG. 2. The nodes are connected by a depthwise separable convolution, a skip connection, and a dilated convolution. In addition to the convolution operations described above, optional convolution operations for node connection may include a depthwise separable convolution with a convolution kernel size of 5, a standard convolution with a convolution kernel size of 3, and a standard convolution with a convolution kernel size of 5. At present, these convolution modes can have good representation for image features in an end-to-end network architecture.

A downsampling output is a channel combination of the four nodes, a convolution step size in the cell is set to 1, and a padding mode is used to make the feature map have a size consistent with that of the input image so as to avoid an information loss.

S2. Constructing a multimodal medical image fusion network, wherein the multimodal medical image fusion network includes a multi-channel DARTS network module, a feature fusion module and an upsampling module. Here, the multi-channel DARTS network module is formed by a plurality of parallel DARTS network architectures. The DARTS network architecture is configured to downsample an input image to obtain a corresponding feature map. The feature fusion module is configured to perform feature fusion on a feature map outputted by a dual-channel DARTS network module. Optionally, in the present invention, the fusion of the feature map is implemented by means of channel combination. Channel combination may perform weighted fusion on features of source images through subsequent convolution. In a case that a network loss function is appropriately designed, the feature fusion implemented by means of channel combination has a better effect, so that useful information of the source images can be retained to a greater extent. The upsampling module is configured to perform convolution upsampling on a fused feature to obtain a fusion result having the same size as the input image. In an upsampling operation, a padding mode with a convolution of 3×3 and a step size of 1 is used to reduce a channel quantity of a convolutional neural network from 128 to 1.

A two-channel DARTS network shown in FIG. 1 is only used as an implementable example for ease of showing the overall structure of the network. According to a quantity of modalities of a fused image, a plurality of parallel channels may further be set.

S3. Training the multimodal medical image fusion network by using the multimodal medical image data through an unsupervised learning method.

To implement network training, the loss function used in the present invention includes SSIM MS-SSIM, edge preservation $Q_p^{s_1 s_2/F}$, SCD, MI, and SR-MI.

In the present invention, the foregoing evaluation indicators are combined in the following manner into a loss function:

$$\text{Loss} = (L_{SCD} + L_{MI}) + \lambda_1 \sqrt[4]{(LSSIM + L_{MS\text{-}SSIM} + L_{Q_p^{s_1 s_2/F}})} + \lambda_2 \cdot L_{SR\text{-}MI}.$$

The foregoing loss function includes three groups of functions: The first group of MI and SCD is related to image grayscale information and a correlation, the second group is related to an image edge and structure information, and the third group is an additional item for constraining an edge, where $\lambda_1$ and $\lambda_2$ are respectively weights of the groups of loss functions.

SCD reflects a sum of correlations of differences between the fused image and the source images, and a calculation formula of SCD is as follows:

$$L_{SCD} = -(R(F-S_2, S_1) + R(F-S_1, S_2))$$

where $S_1$, $S_2$ denote two source images and F denotes the fused result; R represents the calculation of a correlation, and a specific formula is as follows:

$$R(S, F) = \frac{\sum_m \sum_n S_{m,n} F_{m,n}}{\left(\sum_m \sum_n S_{m,n}^2\right)^{\frac{1}{2}} \left(\sum_m \sum_n F_{m,n}^2\right)^{\frac{1}{2}}}$$

MI represents the amount of information of the two sources images included in the fused image, and a specific formula of MI is:

$$L_{MI} = -(MI(S_1, F) + MI(S_2, F))$$

where a formula of the MI is as follows:

$$MI(S, F) = \sum_{f \in F} \sum_{s \in S} p(s, f) \log\left(\frac{p(s, f)}{p(s)p(f)}\right)$$

where p(s) and p(f) are edge distributions, and p(s, f) is a joint distribution of s and f.

A formula of the SSIM loss is as follows:

$$L_{SSIM} = -\frac{SSIM(S_1, F) + SSIM(S_2, F)}{2}$$

where the SSIM is calculated by using information such as brightness, contrast, and structure of two images, and a specific formula is as follows:

$$SSIM(S, F) = \frac{(2\mu_S \mu_F + c_1)(2\sigma_{SF} + c_2)}{(\mu_S^2 + \mu_F^2 + c_1)(\sigma_S^2 + \sigma_F^2 + c_2)}$$

where $\mu_s$ and $\mu_f$ are respectively average values of S and F. $\sigma_S^2$ and $\sigma_F^2$ are respectively variances of S and F, $\sigma_{SF}$ is a covariance of S and F, and $c_1$ and $c_2$ are relatively small constants.

MS-SSIM is an indicator obtained by shrinking an image by different scales with a power of 2 as a factor and then calculating SSIMs on different scales.

$Q_p^{S_1 S_2/F}$ uses a local metric to estimate a preservation degree of significant information (i.e., edge information) from an input in a fused image, and a calculation formula is as follows:

$$L_{Q_p^{S_1 S_2/F}} = -Q_p^{S_1 S_2/F}$$

$$Q_p^{S_1 S_2/F} = \frac{\sum_{n=1}^{N} \sum_{m=1}^{M} Q^{S_1 F}(n, m) w^{S_1}(n, m) + Q^{S_2 F}(n, m) w^{S_2}(n, m)}{\sum_{i=1}^{N} \sum_{j=1}^{M} \left(w^{S_1}(i, j) + w^{S_2}(i, j)\right)}$$

where $Q^{SA_1 F}$ and $Q^{S_2 F}$ respectively represent the degree of preservation of the fused image with respect to edges of the two source images, and a calculation formula thereof is as follows:

$$Q^{SF}(n, m) = Q_g^{SF}(n,m) Q_\alpha^{SF}(n, m)$$

where $Q_g^{SF}$ and $Q_\alpha^{SF}$ respectively represent a length preservation value for an edge and a direction preservation value for an edge, and calculation formulas thereof are as follows:

$$Q_\alpha^{SF}(n, m) = \frac{\Gamma_\alpha}{1 + e^{\kappa_\alpha (A^{SF}(n,m) - \sigma_\alpha)}}$$

$$Q_g^{SF}(n, m) = \frac{\Gamma_g}{1 + e^{\kappa_g (G^{SF}(n,m) - \sigma_g)}}$$

where $\Gamma_\alpha$, $\Gamma_g$, $\kappa_\alpha$, $\kappa_g$, $\sigma_g$, and $\sigma_\alpha$ are constants, and $A^{SF}$ and $g^{SF}$ are respectively a direction related value and a length related value of a source image S and a fused image F, and calculation formulas thereof are as follows:

$$A^{SF}(n, m) = 1 - \frac{|\alpha_S(n, m) - \alpha_F(n, m)|}{\pi/2}$$

$$G^{SF}(n, m) = \begin{cases} \frac{g_F(n, m)}{g_S(n, m)} & \text{if } g_S(n, m) > g_F(n, m) \\ \frac{g_S(n, m)}{g_F(n, m)} & \text{otherwise} \end{cases}$$

where $g_s$, $\alpha_s$, $g_F$, and $\alpha_F$ are respectively edge lengths and angles of the source image and the fused image. In a calculation formula of $Q_p^{S_1 S_2/F}$, $w^{S_1}(n,m) = [g_{S_1}(n,m)]^L$, and $w^{S_2}(n, m) = [g_{S_2}(n, m)]^L$ (where L is a constant), which are used as the weights of the fused image with respect to the edge preservation of the source image for calculating $Q_p^{S_1 S_2/F}$.

SR-MI represents mutual information based on a structural representation result. The structural representation result is obtained by using a principal component analysis network (PCANet).

In the embodiments of the present invention, brain CT and MR images in the data set ATLAS (which comes from the website hosted by Harvard Medical School: http://www.med.harvard.edu/aanlib/home.html, and has collected brain CT, MIll, PET, SPECT images under normal conditions and in different disease states) are chosen, and translated, rotated, and non-rigid transformed, and 30000 pairs of obtained images are used as a training set. In addition, brain CT and MR images that do not belong to the training set are selected to construct a test set, to test the multimodal medical image fusion network.

$$H(X) = \sum_i P(x_i)I(x_i) = -\sum_i P(x_i)\log_b P(x_i)$$

H(X) represents information entropy of an image, $P(x_i)$ represents a probability that a pixel with a grayscale value of i appears, and $I(x_i)$ represents a non-deterministic function of the probability $P(x_i)$.

Fusion evaluation results of the same pair of images in ATLAS using different methods are shown in Table 1. As can be seen from the table, DARTS image fusion has clearly higher SCD, $Q_p^{S_1S_2/F}$, and EN indicators than other methods, and has certain advantages in indicators such as MI and MS_SSIM, indicating that the method has kept information of two source images to a relatively high degree, and has certain advantages in structural aspects such as edge information.

TABLE 1

| Evaluation Indicators | NSCT-SR | DTCWT-SR | NSST-PAPCNN | DenseFuse | VIFNet | Nestfuse | DARTS |
|---|---|---|---|---|---|---|---|
| EN | 5.1348 | 4.9061 | 5.4184 | 4.6565 | 4.7000 | 4.6545 | 5.5156 |
| FMI_pixel | 0.8880 | 0.8980 | 0.8850 | 0.8865 | 0.8895 | 0.8864 | 0.8895 |
| MI | 2.6880 | 2.9077 | 2.6672 | 3.1449 | 3.3285 | 3.3194 | 3.3920 |
| MS_SSIM | 0.5318 | 0.4827 | 0.5746 | 0.5617 | 0.5446 | 0.5865 | 0.5960 |
| $Q_p^{S_1S_2/F}$ | 0.5292 | 0.5257 | 0.5074 | 0.5006 | 0.5254 | 0.4480 | 0.5792 |
| SCD | 1.2110 | 1.1112 | 1.4875 | 1.4059 | 1.1731 | 1.2392 | 1.6352 |

S4. Inputting a multimodal medical image to be fused into a trained multimodal medical image fusion model, to obtain a fusion result.

To prove the superiority of the method in the present invention, a comparative experiment is performed by using six compared algorithms and the method of the present invention. The six compared algorithms are introduced:

1. NSCT-SR: an image fusion algorithm based on the non-subsampled contourlet transform (NSCT) and sparse representation.

2. DTCWT-SR: an image fusion algorithm based on the dual-tree complex wavelet transform (DTCWT) and sparse representation.

3. NSST-PAPCNN: a medical image fusion method based on a parameter adaptive neural network in the non-subsampled shearlet transform (NSCT) field.

4. DenseFuse: an image fusion algorithm that uses a DenseNet-based encoding and decoding structure, performing fusion by using fusion strategies such as addition and L1 regularization.

5. VIFNet: a depthwise learning image fusion method using unsupervised DenseNet encoding and convolutional decoding and a MSE and a weighted SSIM as the loss function.

6. NestFuse: a depthwise learning image fusion method based on a novel NEST network architecture.

Some objective evaluation indicators (EN, FMI_pixel, MI, MS_SSIM, $Q_p^{S_1S_2/F}$, and SCD) are chosen to evaluate a fusion result. In the foregoing evaluation indicators, FMI_pixel represents pixel-level feature MI, and is MI calculation performed based on an image feature. The image feature may be represented by using a gradient, a Sobel edge operator, and the like.

Figure 3A:
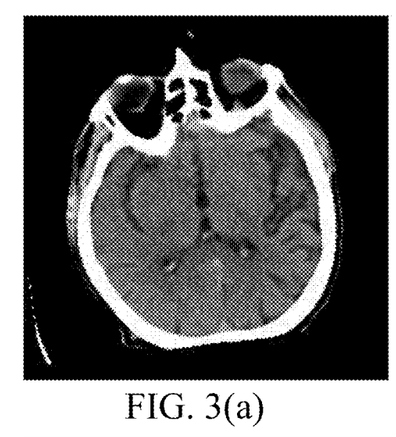
Figure 3B:
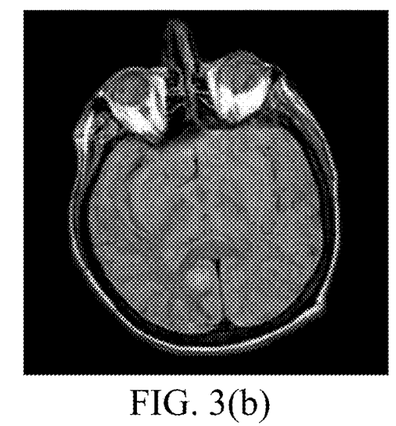
Figure 4A:
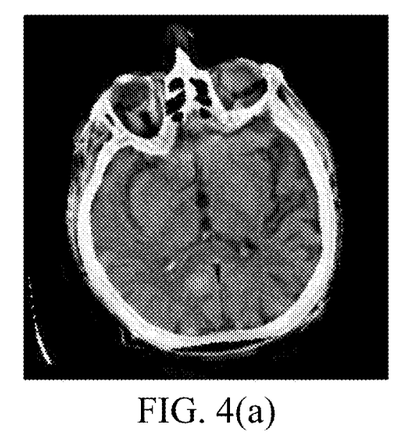
Figure 4B:
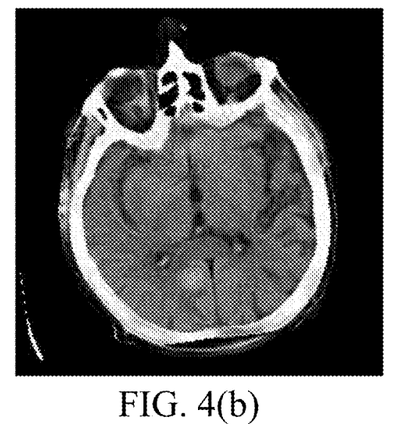
Figure 4C:
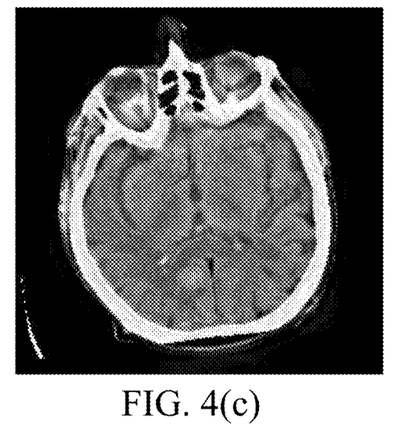
Figure 4D:
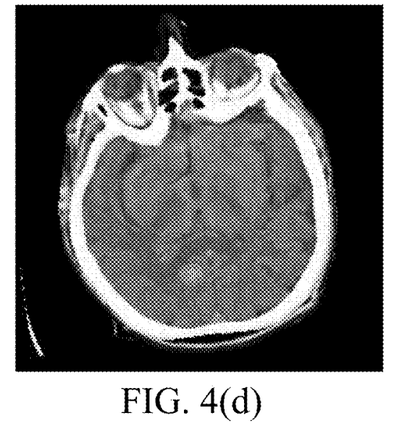
Figure 4E:
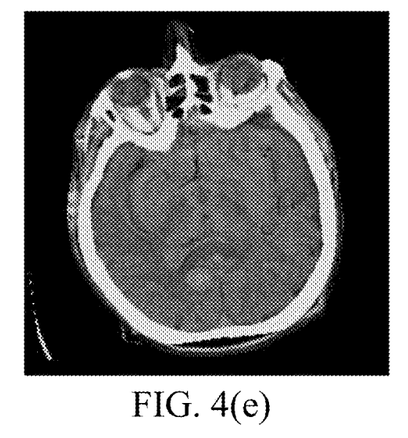
Figure 4F:
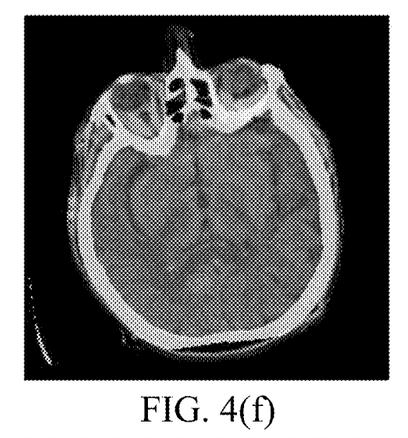
Figure 5:
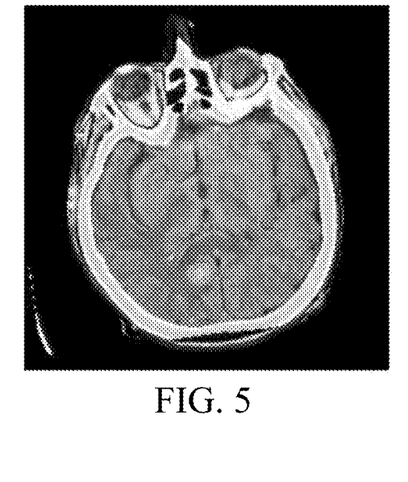
FIG. 5 shows a fused image obtained through the method according to the present invention.

EN (Entropy) represents information entropy. The larger the value of EN is, the richer the information included in an image is. The formula is as follows:

To show the superiority of the present invention to other methods, the embodiments of the present invention further provide diagrams of visual effects of corresponding fused images using the method of the present invention and various compared methods. FIG. 3(a) shows a source CT image. FIG. 3(b) shows a source MR image. FIG. 4(a) shows a fused image obtained by using Compared Method 1. FIG. 4(b) shows a fused image obtained by using Compared Method 2. FIG. 4(c) shows a fused image obtained by using Compared Method 3. FIG. 4(d) shows a fused image obtained by using Compared Method 4. FIG. 4(e) shows a fused image obtained by using Compared Method 5. FIG. 4(f) shows a fused image obtained by using Compared Method 6. And FIG. 5 shows a fused image obtained through the method according to the present invention. As can be seen from the figures, the method in the present invention has excellent performance in the aspect of contrast, and especially has rich details and edge information. This also indicates that the method of the present invention has the advantage that an obtained image has more details and a large amount of information.

It can be easily understood by those skilled in the art that the foregoing description is only preferred embodiments of the present invention and is not intended to limit the present invention. All the modifications, identical replacements and improvements within the spirit and principle of the present invention should be in the scope of protection of the present invention.

The invention claimed is:

1. A multimodal medical image fusion method based on a differentiable architecture search (DARTS) network, the method comprising:

S1. performing a network architecture search on a preset DARTS model by using multimodal medical image data to obtain a DARTS network architecture applicable to the multimodal medical image data, wherein the DARTS network architecture comprises one or more cells connected in series, each cell comprises a plurality of nodes, each of the nodes is connected to outputs of two preceding cells or other nodes in a current cell by means of different convolution operations, and channels of the nodes are combined into an output of the cell;

S2. constructing a multimodal medical image fusion network, wherein the multimodal medical image fusion network comprises a multi-channel DARTS network module, a feature fusion module, and an upsampling module, wherein the multi-channel DARTS network module is formed by a plurality of parallel DARTS network architectures, the DARTS network architecture is configured to downsample an input image to obtain a corresponding feature map, the feature fusion module is configured to perform feature fusion on a feature map outputted by a dual-channel DARTS network module, and the upsampling module is configured to perform convolution upsampling on a fused feature to obtain a fusion image with the same size as the input image;

S3. training the multimodal medical image fusion network by using the multimodal medical image data through an unsupervised learning method; and S4. inputting a multimodal medical image to be fused into a trained multimodal medical image fusion model to obtain a fusion result, wherein structural similarity (SSIM), multi-scale structural similarity (MS-SSIM), edge preservation, sum of the correlations of differences (SCD), mutual information (MI), and structural representation-based mutual information (SR-MI) are used as a loss function for training the multimodal medical image fusion network.

2. The multimodal medical image fusion method based on a DARTS network according to claim 1, wherein the loss function for training the multimodal medical image fusion network is:

$$\text{Loss} = (L_{SCD} + L_{MI}) + \lambda_1 \cdot (L_{SSIM} + L_{MS\text{-}SSIM} + L_{Q_{p}}s_1s_2/F) + \lambda_2 \cdot L_{SR\text{-}MI},$$

wherein $L_{SSIM}$ represents an SSIM loss, $L_{SCD}$ represents an SCD loss, $L_{MI}$ represents an MI loss, $L_{MS\text{-}SSIM}$ represents an MS-SSIM loss, $L_{Q_{p}}s_1s_2/F$ represents an edge preservation loss, $L_{SR\text{-}MI}$ represents an SR-MI loss, and $\lambda_1$ and $\lambda_2$ are respectively weights of the groups of loss functions, respectively.

3. The multimodal medical image fusion method based on a DARTS network according to claim 1, wherein the different convolution operations in step S1 comprise: a depthwise separable convolution with a convolution kernel size of 3, a depthwise separable convolution with a convolution kernel size of 5, a standard convolution with a convolution kernel size of 3, a standard convolution with a convolution kernel size of 5, a dilated convolution with a convolution kernel size of 3, a dilated convolution with a convolution kernel size of 5, and skip connections.

4. The multimodal medical image fusion method based on a DARTS network according to claim 3, wherein the DARTS network architecture comprises one cell.

5. The multimodal medical image fusion method based on a DARTS network according to claim 4, wherein the cell comprises four nodes.

6. The multimodal medical image fusion method based on a DARTS network according to claim 5, wherein a convolution step size in the cell is set to 1, and a padding mode is used to make the feature map have a size consistent with that of the input image.

7. The multimodal medical image fusion method based on a DARTS network according to claim 1, wherein the feature fusion module is configured to perform feature fusion on the feature map outputted by the dual-channel DARTS network module, and specifically fusion of the feature map is implemented by means of channel combination.

8. The multimodal medical image fusion method based on a DARTS network according to claim 1, further comprising performing data augmentation on the multimodal medical image data.

9. The multimodal medical image fusion method based on a DARTS network according to claim 8, wherein the data augmentation comprises translation, rotation, and non-rigid deformation.

10. A multimodal medical image fusion method based on a differentiable architecture search (DARTS) network, the method comprising:

S1. performing a network architecture search on a preset DARTS model by using multimodal medical image data to obtain a DARTS network architecture applicable to the multimodal medical image data, wherein the DARTS network architecture comprises one or more cells connected in series, each cell comprises a plurality of nodes, each of the nodes is connected to outputs of two preceding cells or other nodes in a current cell by means of different convolution operations, and channels of the nodes are combined into an output of the cell;

S2. constructing a multimodal medical image fusion network, wherein the multimodal medical image fusion network comprises a multi-channel DARTS network module, a feature fusion module, and an upsampling module, wherein the multi-channel DARTS network module is formed by a plurality of parallel DARTS network architectures, the DARTS network architecture is configured to downsample an input image to obtain a corresponding feature map, the feature fusion module is configured to perform feature fusion on a feature map outputted by a dual-channel DARTS network module, and the upsampling module is configured to perform convolution upsampling on a fused feature to obtain a fusion image with the same size as the input image;

S3. training the multimodal medical image fusion network by using the multimodal medical image data through an unsupervised learning method; and S4. inputting a multimodal medical image to be fused into a trained multimodal medical image fusion model to obtain a fusion result, wherein the different convolution operations in step S1 comprise: a depthwise separable convolution with a convolution kernel size of 3, a depthwise separable convolution with a convolution kernel size of 5, a standard convolution with a convolution kernel size of 3, a standard convolution with a convolution kernel size of 5, a dilated convolution with a convolution kernel size of 3, a dilated convolution with a convolution kernel size of 5, and skip connections.

11. The multimodal medical image fusion method based on a DARTS network according to claim 10, wherein structural similarity (SSIM), multi-scale structural similarity (MS-SSIM), edge preservation, sum of the correlations of differences (SCD), mutual information (MI), and structural representation-based mutual information (SR-MI) are used as a loss function for training the multimodal medical image fusion network.

12. The multimodal medical image fusion method based on a DARTS network according to claim 11, wherein the loss function for training the multimodal medical image fusion network is:

$$Loss=(L_{SCD}+L_{MI})+\lambda_1 \cdot (L_{SSIM}+L_{MS\text{-}SSIM}+L_{Q_{gs}^1 s_2/F})+\lambda_2 \cdot L_{SR\text{-}MI},$$

wherein $L_{SSIM}$ represents an SSIM loss, $L_{SCD}$ represents an SCD loss, $L_{MI}$ represents an MI loss, $L_{MS\text{-}SSIM}$ represents an MS-SSIM loss, $L_{Q_{gs}^1 s_2/F}$ represents an edge preservation loss, $L_{SR\text{-}MI}$ represents an SR-MI loss, and $\lambda_1$ and $\lambda_2$ are respectively weights of the groups of loss functions, respectively.

13. The multimodal medical image fusion method based on a DARTS network according to claim 10, wherein the DARTS network architecture comprises one cell.

14. The multimodal medical image fusion method based on a DARTS network according to claim 13, wherein the cell comprises four nodes.

15. The multimodal medical image fusion method based on a DARTS network according to claim 14, wherein a convolution step size in the cell is set to 1, and a padding mode is used to make the feature map have a size consistent with that of the input image.

16. The multimodal medical image fusion method based on a DARTS network according to claim 10, wherein the feature fusion module is configured to perform feature fusion on the feature map outputted by the dual-channel DARTS network module, and specifically fusion of the feature map is implemented by means of channel combination.

17. The multimodal medical image fusion method based on a DARTS network according to claim 10, further comprising performing data augmentation on the multimodal medical image data.

18. The multimodal medical image fusion method based on a DARTS network according to claim 17, wherein the data augmentation comprises translation, rotation, and non-rigid deformation.

19. A multimodal medical image fusion method based on a differentiable architecture search (DARTS) network, the method comprising:
- S1. performing a network architecture search on a preset DARTS model by using multimodal medical image data to obtain a DARTS network architecture applicable to the multimodal medical image data, wherein the DARTS network architecture comprises one or more cells connected in series, each cell comprises a plurality of nodes, each of the nodes is connected to outputs of two preceding cells or other nodes in a current cell by means of different convolution operations, and channels of the nodes are combined into an output of the cell;
- S2. constructing a multimodal medical image fusion network, wherein the multimodal medical image fusion network comprises a multi-channel DARTS network module, a feature fusion module, and an upsampling module, wherein the multi-channel DARTS network module is formed by a plurality of parallel DARTS network architectures,
the DARTS network architecture is configured to downsample an input image to obtain a corresponding feature map, the feature fusion module is configured to perform feature fusion on a feature map outputted by a dual-channel DARTS network module, and the upsampling module is configured to perform convolution upsampling on a fused feature to obtain a fusion image with the same size as the input image;
- S3. training the multimodal medical image fusion network by using the multimodal medical image data through an unsupervised learning method; and
- S4. inputting a multimodal medical image to be fused into a trained multimodal medical image fusion model to obtain a fusion result.

* * * * *